United States Patent [19]

Tomalia et al.

[11] 4,261,925
[45] Apr. 14, 1981

[54] SURFACTANTS

[75] Inventors: Donald A. Tomalia; James D. Huffines, both of Midland, Mich.

[73] Assignee: The Dow Chemical Company, Midland, Mich.

[21] Appl. No.: 893,558

[22] Filed: Apr. 5, 1978

Related U.S. Application Data

[63] Continuation-in-part of Ser. No. 775,340, Mar. 7, 1977, abandoned.

[51] Int. Cl.³ .................. C07C 143/74; C07C 143/78; C07C 103/127; C07C 103/132
[52] U.S. Cl. ...................................... 564/94; 252/355; 252/357; 260/404.5; 564/98; 564/182; 564/183; 564/224
[58] Field of Search ............................... 252/355, 357; 260/556 AR, 556 AC, 561 HL, 562 B, 558 R, 561 R, 556 A, 562 R, 404.5 PA

[56] References Cited

U.S. PATENT DOCUMENTS

| | | | |
|---|---|---|---|
| 2,243,329 | 5/1941 | De Groote et al. | 252/357 X |
| 2,340,881 | 2/1944 | Kelley et al. | 260/404.5 PA X |
| 2,765,325 | 10/1956 | Niederhauser | 260/561 R X |
| 3,676,483 | 7/1972 | Hu | 260/558 R X |
| 3,687,870 | 8/1972 | Muzyczko et al. | 260/556 AR X |
| 4,120,804 | 10/1978 | Smith et al. | 252/47.5 |
| 4,152,342 | 5/1979 | Kelyman et al. | 260/561 R X |

OTHER PUBLICATIONS

Seeliger et al.: "Recent Syntheses and Reactions of Cyclic Imidic Esters," Angew. Chem. Internat. Edit., vol. 5 (1966), No. 10, pp. 875, 880, 881.

*Primary Examiner*—Richard D. Lovering
*Attorney, Agent, or Firm*—Joyce P. Hill; Michael L. Glenn; L. Wayne White

[57] ABSTRACT

Surfactants having an HLB of from about 12 to about 20, preferably 14 to about 20, are disclosed which correspond to formulas I and II:

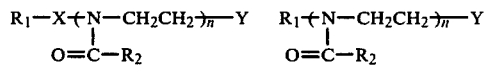

wherein:

$R_1$ is a nonpolymerizable hydrocarbyl or inertly-substituted hydrocarbyl group of at least 8 carbon atoms; $R_2$ is hydrogen or alkyl; X is

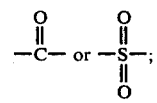

Y is a terminal inorganic or organic group; and n is at least 2.

18 Claims, No Drawings

SURFACTANTS

CROSS-REFERENCE TO RELATED APPLICATION

This is a continuation-in-part of U.S. patent application Ser. No. 775,340 filed Mar. 7, 1977, and now abandoned, the disclosure of which is incorporated herewith by reference.

BACKGROUND OF THE INVENTION

This invention pertains to novel surfactants. The hydrophilic portion of the molecule is a linear, acylated polyethylenepolyamine. The hydrophobic portion of the molecule is a hydrocarbyl or an inertly-substituted hydrocarbyl group of at least 8 carbon atoms. The length of the hydrocarbon chain also determines the oil solubility of the polymer product; the more carbon atoms in the chain, the more soluble the product in oil. These compounds are non-ionic surfactants having an HLB of from about 12 to about 20, preferably from 14 to about 20, and range from water soluble (or dispersible) to oil soluble compounds.

The literature is replete with information pertaining to surfactant molecules in general and non-ionic surfactants in particular. See the handbook entitled "McCutcheon's Detergents and Emulsifiers", published annually by the Allured Publishing Corporation, and see also the Surfactant Science Series. Volume One of this series is entitled "Non-Ionic Surfactants", edited by M. J. Schick and published in 1967. This volume explains the concept of hydrophilic-lypophilic-balance (HLB) and methods of determining same for non-ionic surfactants.

Surfactants have many uses as emulsifiers, detergents, etc., and, the term surfactant as here used means compounds which reduce the surface tension of water when dissolved in water or aqueous solutions, or which reduce interfacial tension between two normally immiscible liquids (e.g., oil and water).

SUMMARY OF THE INVENTION

A novel class of surfactants has been discovered having an HLB of from about 12 to about 20, preferably 14 to about 20, and which correspond to formulas I and II:

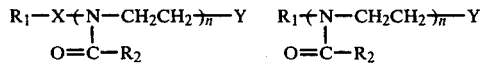

wherein:

$R_1$ is a nonpolymerizable hydrocarbyl or inertly-substituted hydrocarbyl group of at least 8 carbon atoms and is preferably a hydrocarbyl group of from 8 to about 100 carbon atoms and, more preferably, is an alkylbenzyl or alkylphenyl group, or long chain aliphatic hydrocarbon group of from 8 to about 100 carbon atoms. A hydrocarbyl group having from 8 to about 20 carbon atoms or an alkylbenzyl or alkylphenyl group of from 8 to about 20 carbon atoms are the most preferred $R_1$ substituents.

$R_2$ is hydrogen or an alkyl group of from 1 to about 18 carbon atoms and is preferably hydrogen or lower alkyl of from 1 to 4 carbon atoms and is more preferably hydrogen, methyl or ethyl.

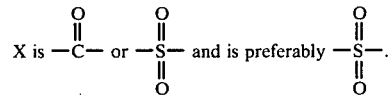

Y is a terminal inorganic or organic group and is preferably chloro, bromo, iodo or hydroxy.

n is at least 2 and is varied to give sufficient polyethylenepolyamide groups to render the molecule water-soluble or water-dispersible and sufficient to provide an HLB of from about 12 to about 20, preferably 14 to about 20. Normally, n will be a value of from 2 to about 40 preferably n is from 3 to 10 or n is from 4 to 10.

The surfactants represented by formulas I and II are water-soluble, water-dispersible, or water-and-oil soluble materials which are normally viscous liquids or low melting solids. Such compounds are conveniently prepared by reacting (1) a hydrocarbon or an inertly-substituted hydrocarbon bearing a displaceable halo group (e.g., chloro, bromo or iodo) or a hydrocarbon or inertly-substituted hydrocarbon capped with a carboxylic or sulfonic acid group, or capped with a carboxylic or sulfonic acid halide group, or capped with an ethylenically unsaturated dicarboxylic acid or anhydride (e.g., maleic or succinic acid or anhydride) with (2) an oxazoline corresponding to the formula:

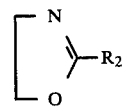

The reactants used in the above process are known classes of compounds having many members.

The hydrocarbons bearing a displaceable halo group include aliphatic, aromatic and cycloaliphatic hydrocarbons bearing chlorine, bromine or iodine and compounds having a mixture of aliphatic, aromatic and/or cycloaliphatic hydrocarbon groups bearing chlorine, bromine or iodine. Of these, the alkylbenzyl halides are preferred. Examples of suitable such compounds include chlorinated polyisobutylenes, iodonapthylene, propylcyclohexyl bromide, butylbenzyl bromide, dodecylbenzyl chloride, etc. Such compounds react with oxazolines of formula III to give surfactants of formula II.

The hydrocarbyl or inertly-substituted hydrocarbyl compounds may also bear carboxylic or sulfonic acid groups, carboxylic or sulfonic acid halide groups, or carboxylic acid anhydride groups which are reactive with the oxazolines. Such compounds may likewise be aliphatic, aromatic or cylcoaliphatic compounds (or mixtures thereof) bearing the indicated functional moieties. Examples of such compounds include octanoic acid, dodecanoic acid, stearic acid, etc., and the corresponding acid chlorides and the corresponding compounds bearing a sulfonic acid or sulfonic acid halide in place of the carboxylic acid or carboxylic acid halide moiety. Other examples include the polyolefins (e.g., polyisobutylenes) end capped with an α,β-ethylenically unsaturated mono or dicarboxylic acid (e.g., acrylic acid, maleic acid, itaconic acid, succinic anhydride, etc.). Such compounds may be prepared by a variety of well-known techniques. See, for example, U.S. Pat. Nos. 3,448,048, 3,697,428, 3,948,800 and 3,941,834. Of these, the hydrocarbyl compounds bearing a sulfonic acid halide group are the preferred reactants and of these, the alkylphenyl sulfonic acid halides are more preferred. Examples of suitable such compounds include dodecylphenyl sulfonyl chloride, polyisobutylene sulfonyl chloride, etc. Such compounds react with oxazolines of formula III to give surfactants of formula I.

The oxazolines of formula III are likewise well-known. The oxazoline monomers are typically prepared from N-2-hydroxyethylcarboxamides by techniques set forth in the following review articles:

(a) Wiley, et al., *Chemical Reviews*, Vol. 44, 447 (1949);
(b) Seeliger, et al., *Angew. Chem. Internat. Edit.*, Vol. 5, 10 (1966); and
(c) Frump, *Chemical Reviews*, Vol. 71, 5 (1971).

See also patents classified by the U.S. Patent and Trademark Office under 260/307F. Examples of suitable such oxazoline reactants include those of formula III wherein $R_2$ is hydrogen, methyl, ethyl, propyl, amyl, heptyl, nonyl, undecyl, octadecyl, etc.

The reaction of the oxazolines with the hydrophobic molecules bearing displaceable halo groups, etc., is conducted by merely blending the reactants and warming the reaction mixture at an elevated temperature sufficient to promote the grafting polymerization reaction. Typical reaction temperatures will range from about 50° C. to about 150° C., depending upon the choice of reactants. The amount of 2-oxazoline (III) can be varied so as to give products having the desired number of ring-opened oxazoline units per hydrophobic unit.

The following examples will further illustrate the invention.

EXPERIMENTAL

EXAMPLES 1-4

Dodecylphenyl sulfonyl chloride was reacted with 2-ethyl-2-oxazolline in ratios so as to achieve compounds having 3, 5, 7 or 10-ring-opened oxazoline units per molecule. The reaction was conducted by blending the reactants and warming the mixture overnight at 90° C. The products were thus obtained in approximately a 75-80 percent yield as a mixture with poly(2-ethyl-2-oxazoline). The reaction products had HLB values of from 17 to 20.

EXAMPLE 5

Brominated polyisobutylene having a molecular weight of about 225 was reacted with ten equivalents of 2-ethyl-2-oxazoline in the presence of a catalytic amount of potassium iodide in dimethylformamide solvent. The reaction was conducted under a nitrogen blanket for approximately 3 hours. The dimethylformamide solvent was removed under reduced pressure leaving a viscous material which formed an emulsion with water and was insoluble in hexane.

EXAMPLES 6-9

Dodecylbenzyl chloride was reacted with 2-ethyl-2-oxazoline in the presence of a catalytic amount of potassium iodide under substantially the same conditions as Example 5. The amount of 2-ethyl-2-oxazoline was varied so as to give a product having 4, 6, 8 or 10 ring-opened oxazoline units per dodecylbenzyl chloride group. These compounds had HLB values of from 14 to about 18. Similar results are achieved using dodecylbenzyl bromide in place of dodecylbenzyl chloride in this reaction.

EXAMPLE 10

Octanoyl chloride was reacted with 2-ethyl-2-oxazoline for 16 hours at 90° C. The ratio of reactants was calculated to add 10 ring-opened oxazoline units per carboxylic acid chloride molecule. The reaction product had an HLB of approximately 20.

EXAMPLES 11-15

0.04 Moles of polyisobutylene sulfonyl chloride were reacted with 0.2 moles of 2-ethyl-2-oxazoline in tetrachloroethylene solvent. The reaction was conducted under a nitrogen blanket for approximately 4 hours. The tetrachloroethylene solvent was evaporated and the polyisobutylene (PIB)-polyethyloxazoline product was extracted with hexane. PIB-polyethyloxazoline is a brown solid which is soluble in hexane and also forms a solution in water. Nuclear magnetic resonance spectroscopy analysis of the product revealed 5 moles of oxazoline per mole of PIB. The reaction product had an HLB of approximately 16. In substantially the same manner as described above, polyisobutylene sulfonyl chloride, having an average molecular weight of from about 225 to about 2000, is reacted with varied amounts of 2-ethyl-2-oxazoline so as to achieve compounds having 3, 7, or 10 ring-opened oxazoline units per molecule. The reaction products had HLB values of from 12 to 20.

Other surfactants of formulas I and II can be prepared by the appropriate choice of reactants as set forth above.

We claim:

1. A surfactant having a hydrophilic-lypophilic-balance (HLB) of from about 12 to about 20 and corresponding to formula I:

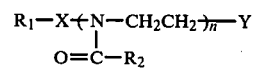

wherein:
$R_1$ is a nonpolymerizable hydrocarbyl or inertly-substituted hydrocarbyl group of at least 8 carbon atoms;
$R_2$ is hydrogen or alkyl of from 1 to about 18 carbon atoms;
X is

Y is chloro, bromo, or iodo; and
n is at least 2 and is varied to achieve the desired HLB.

2. A surfactant having a hydrophilic-lypophilic-balance (HLB) of from about 12 to about 20 and corresponding to formula I:

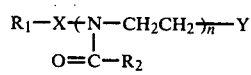

wherein:
$R_1$ is a nonpolymerizable hydrocarbyl or inertly-substituted hydrocarbyl group of at least 8 carbon atoms;

$R_2$ is hydrogen or alkyl of from 1 to about 18 carbon atoms;

X is

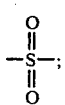

Y is chloro, bromo, iodo or hydroxy; and n is at least 2 and is varied to achieve the desired HLB.

3. The compound defined by formula I in claim 2 wherein $R_1$ is dodecylphenyl; $R_2$ is ethyl; Y is chloro; and n is from 3 to 10.

4. The compound defined by formula I in claim 2 wherein $R_1$ is polyisobutylene having an average molecular weight of from about 225 to about 2000; $R_2$ is ethyl; X is

Y is chloro; and n is from 3 to 10.

5. A surfactant having a hydrophilic-lypophilic-balance (HLB) of from about 12 to about 20 and corresponding to formula II:

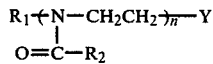

wherein:
$R_1$ is a nonpolymerizable hydrocarbyl or inertly-substituted hydrocarbyl group of at least 8 carbon atoms;

$R_2$ is hydrogen or alkyl of from 1 to about 18 carbon atoms;

Y is chloro, bromo, iodo or hydroxy; and n is at least 2 and is varied to achieve the desired HLB.

6. The compound defined by formula II in clalim 5 wherein $R_1$ is dodecylbenzyl; $R_2$ is ethyl; Y is chloro or bromo; and n is from 4 to 10.

7. The surfactant as defined by claim 5, wherein Y is chloro or bromo.

8. The compound defined by claim 1, 2 or 5 wherein $R_1$ is a hydrocarbyl group having from 8 to about 100 carbon atoms.

9. The compound defined by claim 8 wherein $R_1$ is an alkylbenzyl or alkylphenyl group of from 8 to about 100 carbon atoms.

10. The compound defined by claim 1, 2 or 5 wherein $R_2$ is hydrogen or lower alkyl of from 1 to 4 carbon atoms.

11. The compound defined by claim 10 wherein $R_2$ is hydrogen, methyl or ethyl.

12. The compound defined by claim 1, 2 or 5 wherein n is from 2 to about 40.

13. The compound defined by claim 1, 2 or 5 wherein the hydrophilic-lypophilic-balance is from about 14 to about 20.

14. The compound defined by claim 13 wherein $R_1$ is a hydrocarbyl group having from 8 to about 20 carbon atoms.

15. The compound defined by claim 13 wherein $R_1$ is an alkylbenzyl or alkylphenyl group of from 8 to about 20 carbon atoms.

16. The compound defined by claim 13 wherein $R_2$ is hydrogen or lower alkyl of from 1 to 4 carbon atoms.

17. The compound defined by claim 16 wherein $R_2$ is hydrogen, methyl or ethyl.

18. The compound defined by claim 13 wherein n is from 2 to about 40.

* * * * *